(12) United States Patent
Yogo et al.

(10) Patent No.: US 6,327,506 B1
(45) Date of Patent: Dec. 4, 2001

(54) FAR INFRARED HEATING APPARATUS

(76) Inventors: Teruaki Yogo, 2-601-1113, Shikenya, Moriyama-ku, Nagoya-shi, Aichi-ken (JP); Akira Nakashima, 13, Shirasaka-cho, Seto-shi, Aichi-ken (JP)

( * ) Notice: Subject to any disclaimer, the term of this patent is extended or adjusted under 35 U.S.C. 154(b) by 0 days.

(21) Appl. No.: 09/368,235

(22) Filed: Aug. 4, 1999

(30) Foreign Application Priority Data

Apr. 14, 1999 (JP) .................................................. 11-106730

(51) Int. Cl.[7] .................................................... A61F 2/00
(52) U.S. Cl. ................ 607/100; 607/90; 607/96; 607/88; 606/27; 606/31; 128/898
(58) Field of Search .................. 607/88, 89–91, 607/93, 96, 2, 100–102; 362/313; 606/10–13, 27, 8, 9; 128/898

(56) References Cited

U.S. PATENT DOCUMENTS

| | | | |
|---|---|---|---|
| 4,316,467 | * 2/1982 | Muckerheide | 128/303.1 |
| 4,672,969 | * 6/1987 | Dew | 128/397 |
| 4,976,706 | * 12/1990 | Aki et al. | 604/304 |
| 5,107,126 | * 4/1992 | Yano | 250/493.1 |
| 5,140,984 | * 8/1992 | Dew et al. | 128/395 |
| 5,220,927 | * 6/1993 | Astraham et al. | 128/785 |
| 5,354,323 | * 10/1994 | Whitebook | 607/89 |
| 5,409,479 | * 4/1995 | Dew et al. | 606/11 |
| 5,459,327 | * 10/1995 | Nomura | 250/504 R |
| 6,004,344 | * 12/1999 | Fujii | 607/91 |
| 6,033,431 | * 3/2000 | Segal | 607/89 |

FOREIGN PATENT DOCUMENTS 951912   8/1991   (JP) .

* cited by examiner

Primary Examiner—Linda C. M. Dvorak
Assistant Examiner—Ahmed Farah
(74) Attorney, Agent, or Firm—Davis & Bujold, P.L.L.C.

(57) ABSTRACT

A far infrared heating methods to facilitate a user receiving continued comfortable thermal stimulation. The far infrared heating method, are provided with a temperature sensor for attachment to the object to be heated, and when the temperature detected by the temperature sensor has reached a predetermined maximum temperature, the radiation from the far infrared radiator is stopped. Furthermore, the user can switch to a timer control mechanism which causes the far infrared radiator to radiate intermittently during a predetermined time cycles.

18 Claims, 7 Drawing Sheets

FAR INFRARED HEATING APPARATUS

FIELD OF THE INVENTION

The invention relates to a far infrared heating apparatus which is particularly suitable for a far infrared radiation treatment apparatus for medical or health preservation purposes.

BACKGROUND OF THE INVENTION

Conventionally, various kinds of infrared radiation treatment apparatuses, using thermal effects, have been utilized for purposes such as relieving lower back pain or a stiff neck. Infrared rays are classified by their wavelengths generally as near infrared rays, far infrared rays and the like.

Near infrared rays, which cause electromagnetic wave damage like cataracts, sunstroke, and cytoclasis, must be reduced as much as possible when infrared rays are utilized for medical treatment. In contrast, due to far infrared rays significant thermal and wave motion effects (resonance (vibration) absorption phenomenon), they are not only harmless to humans but they also promote metabolism by promoting blood circulation in capillaries and they activate the automatic functions of the nervous and hormone systems, thereby activating the functions of the immune system and the spontaneous recovery system.

Radiotherapy also uses radiation which is a kind of electromagnetic wave and is employed in medical facilities particularly because it is effective in killing cancer cells. However, radiotherapy causes side effects, such as a swollen face and pain, because the radiation also damages the surrounding normal cells.

Therefore, far infrared radiation treatment apparatuses recently have become an alternative to radiotherapy apparatuses. The publication of Unexamined Japanese Utility Model Application No Hei 3-51912 discloses a far infrared heating apparatus comprising a radiator, which is made by winding a heating wire around a hollow ceramic cylinder to radiate far infrared rays.

However, conventional apparatuses, like the above, place great importance on simply heating an object to be heated by the radiating infrared rays. This results in the following problem when infrared rays are applied for the treatment of cancer and the like. During cancer treatment, cancer cells are killed by means of the heat-shock protein effect in the patient's body caused by heating the affected part (e.g. the object to he heated). When the affected part is maintained at a certain temperature, however, the part becomes used to the thermal stimulation and the heat-shock protein effect cannot be fully maximized.

SUMMARY OF THE INVENTION

Wherefore, a major object of the invention is to provide a far infrared heating apparatus which continues providing thermal stimulation so that the heat-shock protein effect on the object to be heated can be further heightened.

Another object of the invention is to provide a far infrared heating apparatus with a temperature sensor to be attached to an object to be heated. A sensor control which stops, for a predetermined period of time, radiation from the far infrared radiator when the temperature detected by the temperature sensor equals or exceeds a predetermined temperature.

A further object of the invention is to provide a timer control for radiating infrared rays intermittently from the far infrared radiator during a predetermined cycle. Also, a switching means for switching between the sensor control and the timer control as desired.

A still further object of the invention is to provide a bobbin around which a heating wire is wound and a ceramic coating applied to the exterior surface of the bobbin and the wire.

Yet still another object of the invention is to heat the object to be heated up to a maximum temperature and then cool the object to be heated by stopping the heating for a predetermined period of time. The object to be heated is then again heated, once the predetermined period of time has elapsed, until the object to be heated again reaches the maximum temperature. Due to this cycling "on" and "off", the object to be heated feels this as a "fluctuation" in heat and, therefore, does not become used to the thermal stimulation thereby allowing the user to obtain an adequate heat-shock protein effect by using oscillating temperature. Thus, the invention can be applied to an apparatus for cancer treatment as well as for alleviating any sharp pain caused by cancer. Also, the user (the object to be heated) can undergo desired treatment by switching between the sensor control and the timer control.

BRIEF DESCRIPTION OF THE DRAWINGS

The invention will now be described, by way of example, with reference to the accompanying drawings, in which.

DETAILED DESCRIPTION OF THE PREFERRED EMBODIMENT

Figure 1:
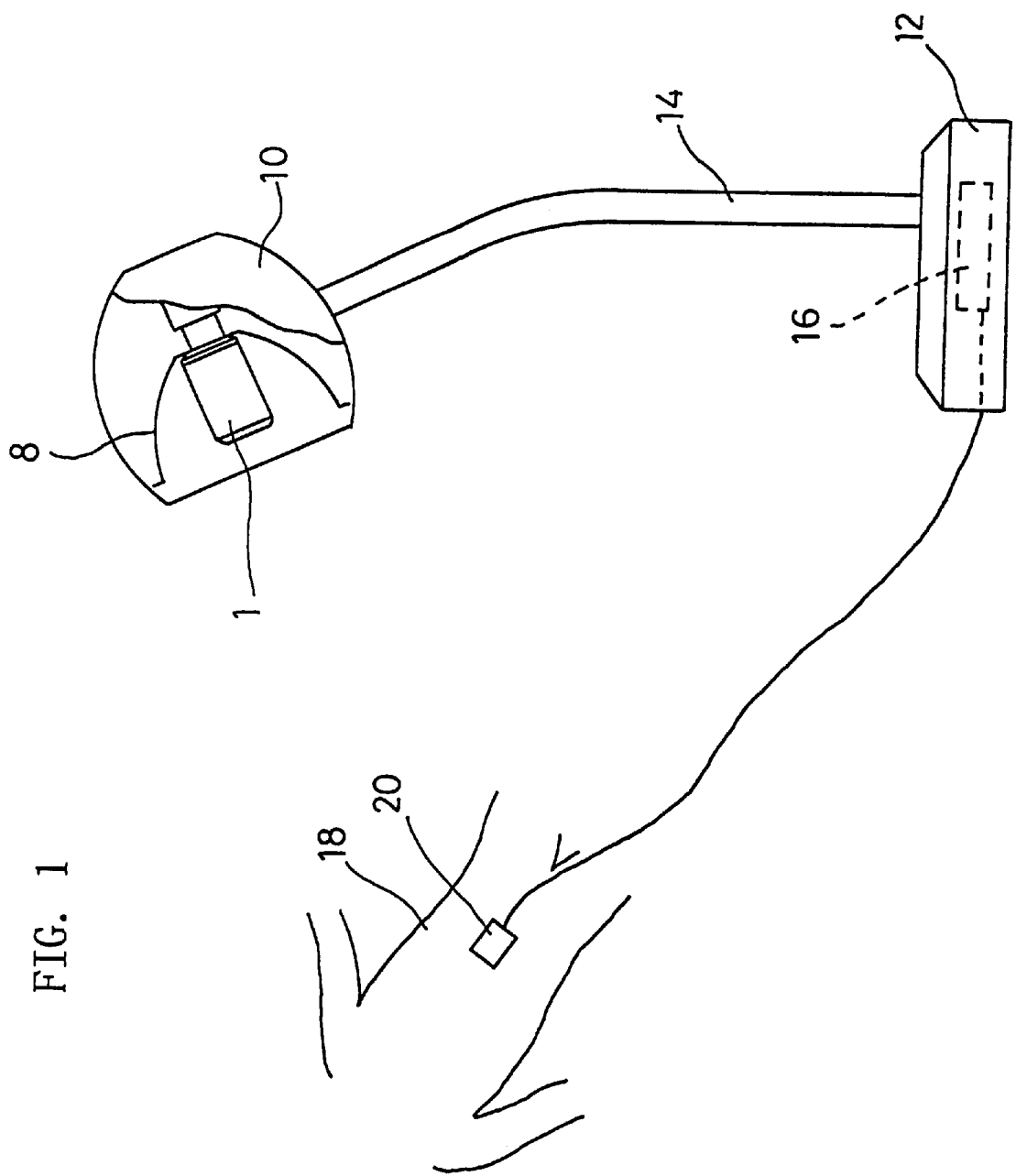
FIG. 1 is a schematic view showing a construction of a far infrared heating apparatus, according to a preferred embodiment of the present invention.
Figure 2:
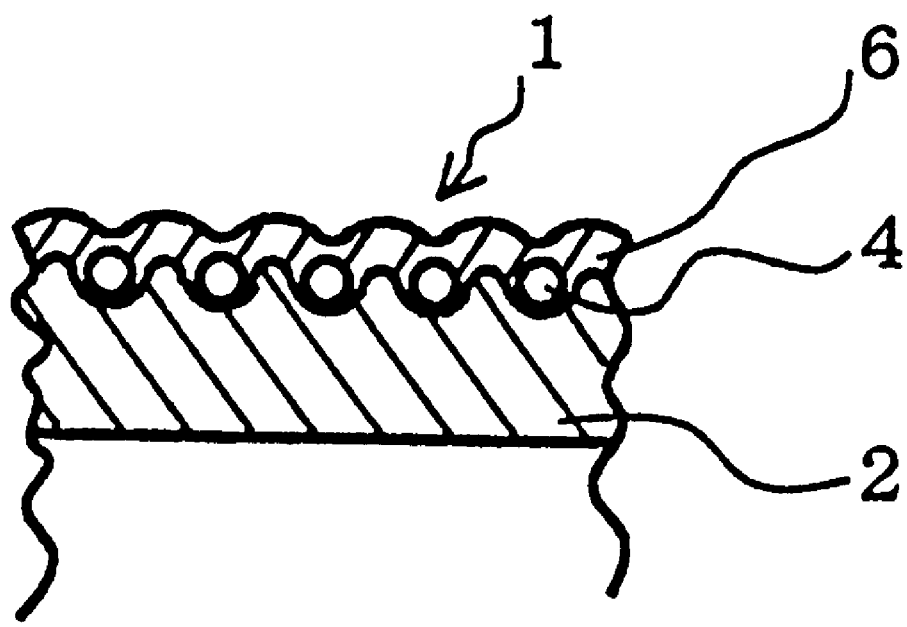
FIG. 2 is an enlarged partial sectional view of a far infrared radiator of the preferred embodiment.

As shown in FIG. 1, a far infrared heating apparatus is provided with a far infrared radiator 1. As shown in FIG. 2, the far infrared radiator 1 comprises a heating wire 4 wound around a tubular ceramic bobbin 2 and the exterior surfaces thereof are coated with a ceramic 6. When the heating wire 4 is heated by the current flowing therethrough, the far infrared radiator 1 radiates far infrared rays having a wavelength of about 4 microns or more The far infrared radiator 1, to which a reflective shade 8 is attached, is accommodated within a top housing 10 The top housing 10 is secured to a base 12 by a flexible support 14. A control circuit 16 is contained within the base 12 and coupled to the far infrared radiator by at least one wire (not shown).

Figure 3:
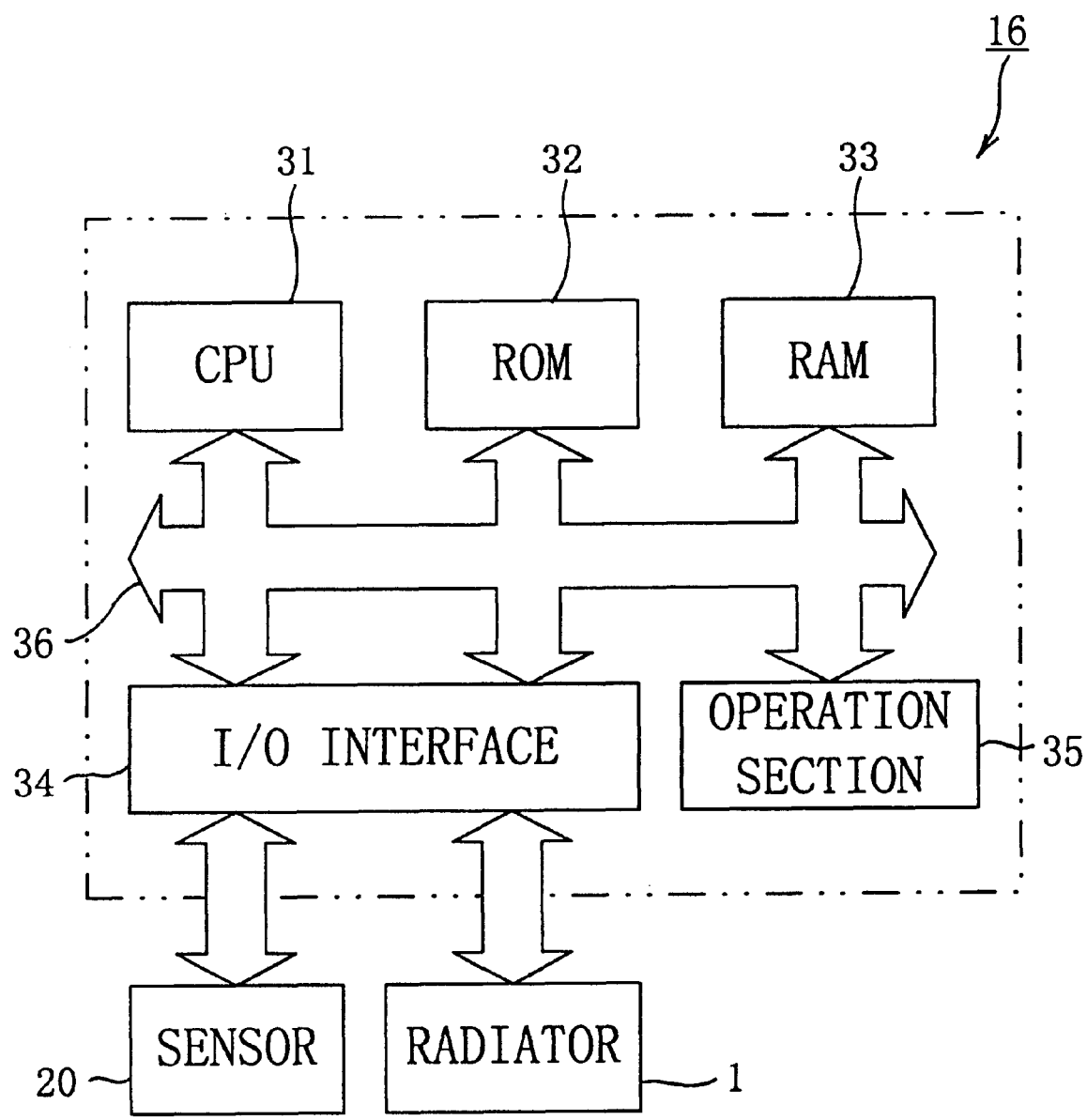
FIG. 3 is a block diagram showing an example of the control circuit of the preferred embodiment.

The control circuit 16 controls heating of the heating wire 4 by connecting/disconnecting the power supply to the heating wire 4. As schematically illustrated in FIG. 3, the control circuit 16 comprises a CPU 31 for controlling the radiation process, a ROM 32 for storing main control programs and the like, a RAM 33 for temporarily storing information, including the control conditions set by an operation section 35, and an input/output interface 34 for conveying data and information between those components and the radiator 1 and a temperature sensor 20. All of these components are connected to communicate with one another by means of a communication bus 36.

The radiation process has the feature that radiation is performed intermittently To control the radiation, two modes of operation, namely, a timer control process and a sensor control process, are available and a user selects one of the two modes of operation via an operation section 35.

When the user chooses the timer control process, the user also presets the control conditions, such as a total intermittent connecting time and a connecting cycle. The total intermittent connecting time here means the total time, 20 minutes or 30 minutes for example, during which the current is intermittently supplied to the far infrared radiator 1 for use in the radiation process, The connecting cycle consists of a connecting time, during which the current to the far infrared radiator 1 is "on" and a disconnecting time during which the current is "off". Both the connecting time and the disconnecting time are set for 1 to 3 minutes, for example.

When the user chooses the sensor control process, the user also presets the control conditions, such as a maximum temperature and a disconnecting time, via the operation section 35. The maximum temperature here means the upper limit of temperature for the object to be heated 18. And the disconnecting time means the time period during which the current supplied to far infrared radiator 1 is "off".

The CPU 31 detects the preset state of the operation section 35, and stores the data indicating the preset control conditions in the RAM 33. Then, the CPU reads the data ind executes the control programs stored in ROM 32.

The specific processes performed by CPU 31 will be explained hereinafter with reference to FIGS. 4 through 6.

Figure 4:
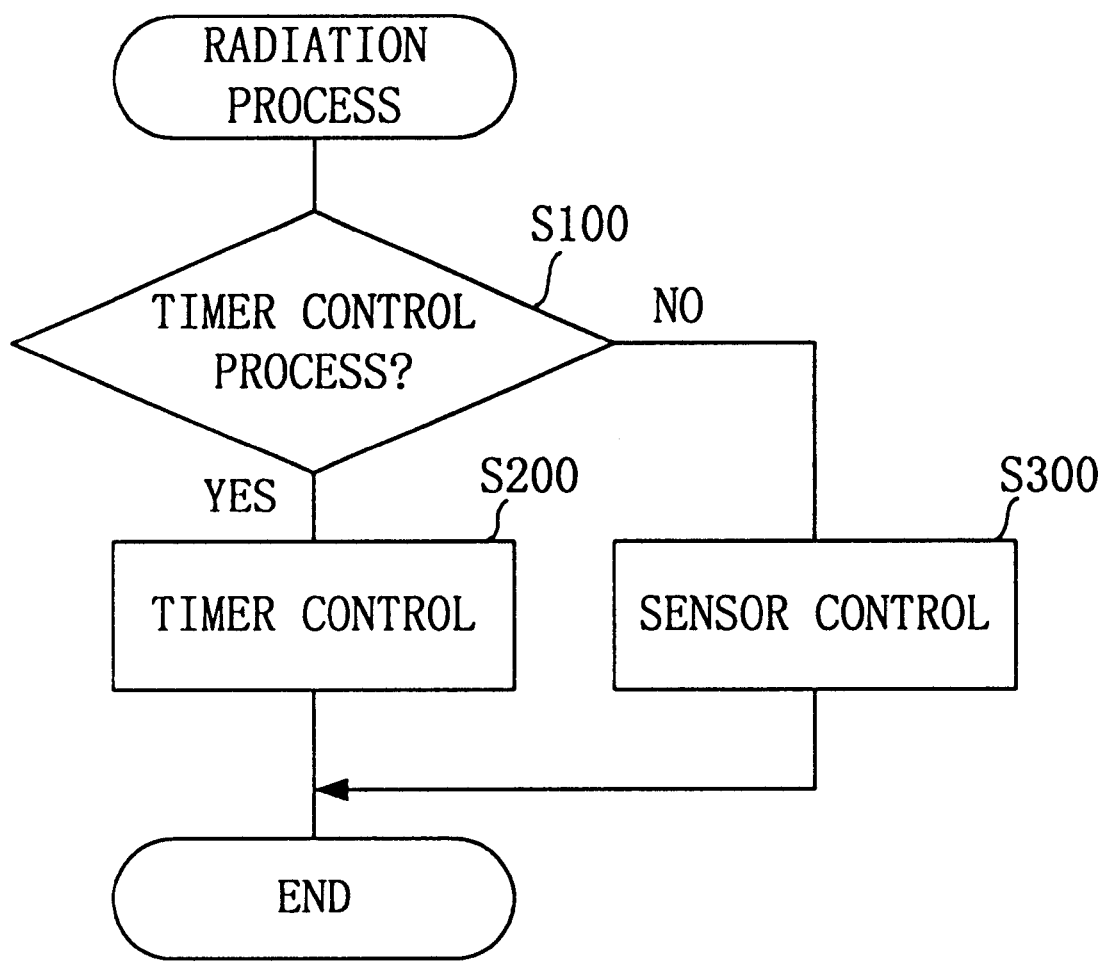
FIG. 4 is a flow chart showing an example of the radiation process performed in the control circuit of the preferred embodiment.

As shown in FIG. 4, when the power supply is turned "on", the CPU 31 in the control circuit 16 determines whether or not the process mode is set for the timer control process (Step 100). If it is determined that the timer control process has been selected, the timer control process is performed (Step 200). If it is determined that the sensor control process has been selected, the sensor control process is performed (Step 300).

Figure 5:
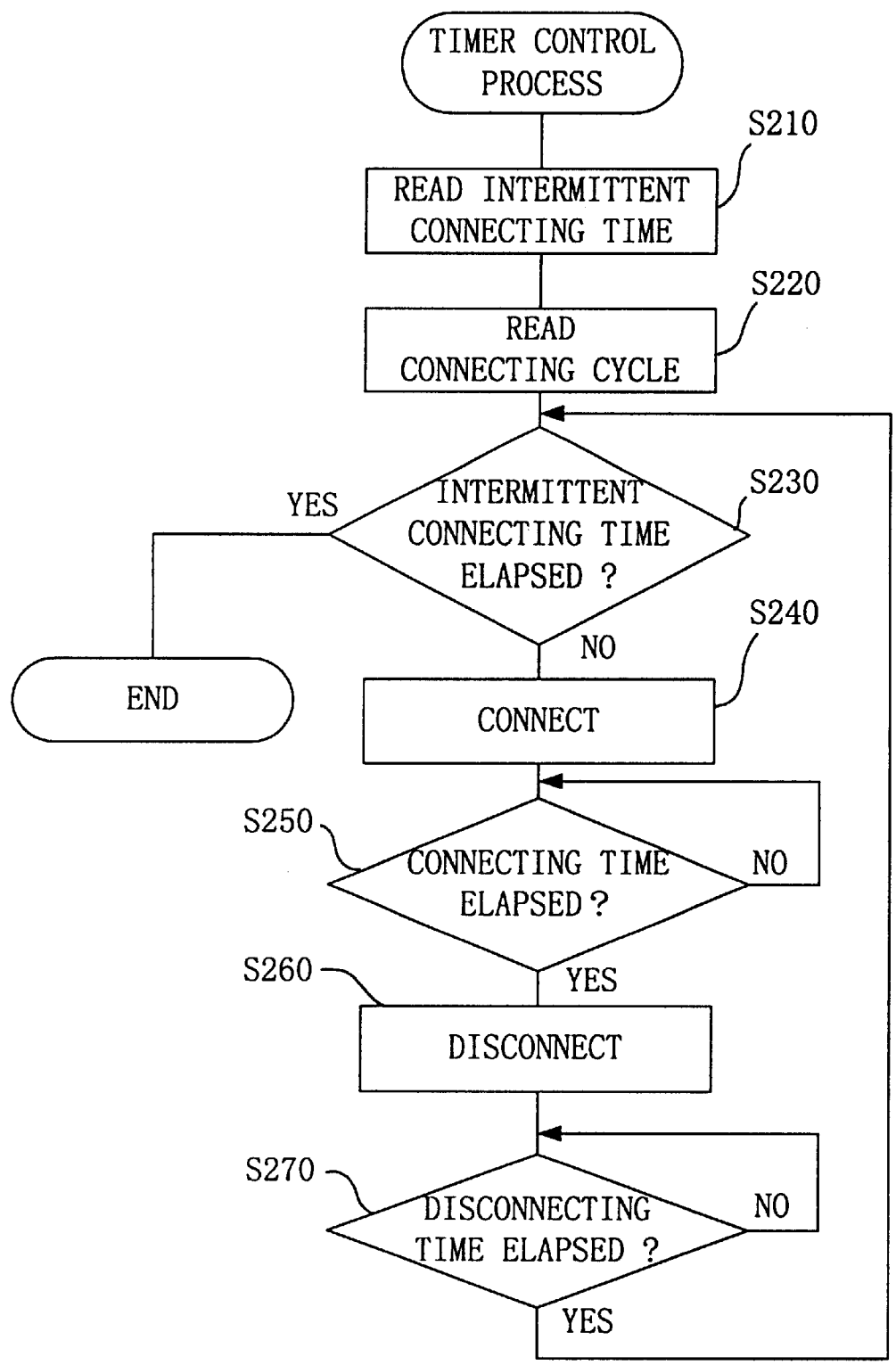
FIG. 5 is a flow chart showing an example of the timer control process performed in the control circuit of the preferred embodiment.

In the timer control process, as shown in FIG. 5, the CPU 31 firstly reads a predetermined total intermittent connecting time stored in RAM 32 (Step 210).

Secondly, the CPU 31 also reads a predetermined connecting cycle during which the current to the far infrared radiator 1 is intermittently "on" (Step 220).

Thirdly, it is determined whether or not the predetermined total intermittent connecting time, read at Step 210, has elapsed (Step 230). If it is determined that the predetermined total intermittent connecting time has not elapsed, the current to far infrared radiator 1 is turned "on" (Step 240). Then, far infrared rays are radiated from the far infrared radiator 1 toward the object to be heated 18.

Next, it is determined whether or not a predetermined connecting time has elapsed (Step 250). If it is determined that the predetermined connecting time has not elapsed, the current to the far infrared radiator 1 is kept "on".If it is determined that the predetermined connecting time has elapsed, the current to the far infrared radiator 1 is shut "off" (Step 260).

In turn, it is determined whether or not a predetermined disconnecting time has elapsed (Step 270). If it is determined that the predetermined disconnecting time has not elapsed, the current is kept "off". If it is determined that the predetermined disconnecting time has elapsed, the processes returns to Step 230 and repeats the process. Thus, the far infrared radiator 1 radiates far infrared rays toward the object to be heated 18 during the connecting time, while the radiation is prevented from radiating far infrared rays toward the object to be heated 18 during the disconnecting time.

Since heating during the connecting time and the stopping of heating during the disconnecting time are repeated by the far infrared radiator 1, the object to be heated 18 repeatedly undergoes heating and cooling. The object to be heated 18 (e.g the user) feels this as a fluctuation in heat so that the user can continue undergoing treatment comfortably without becoming used to the thermal stimulation. When it is determined, at Step 230, that the predetermined total intermittent connecting time has elapsed, the current is shut "off" and the control process ends.

Figure 6:
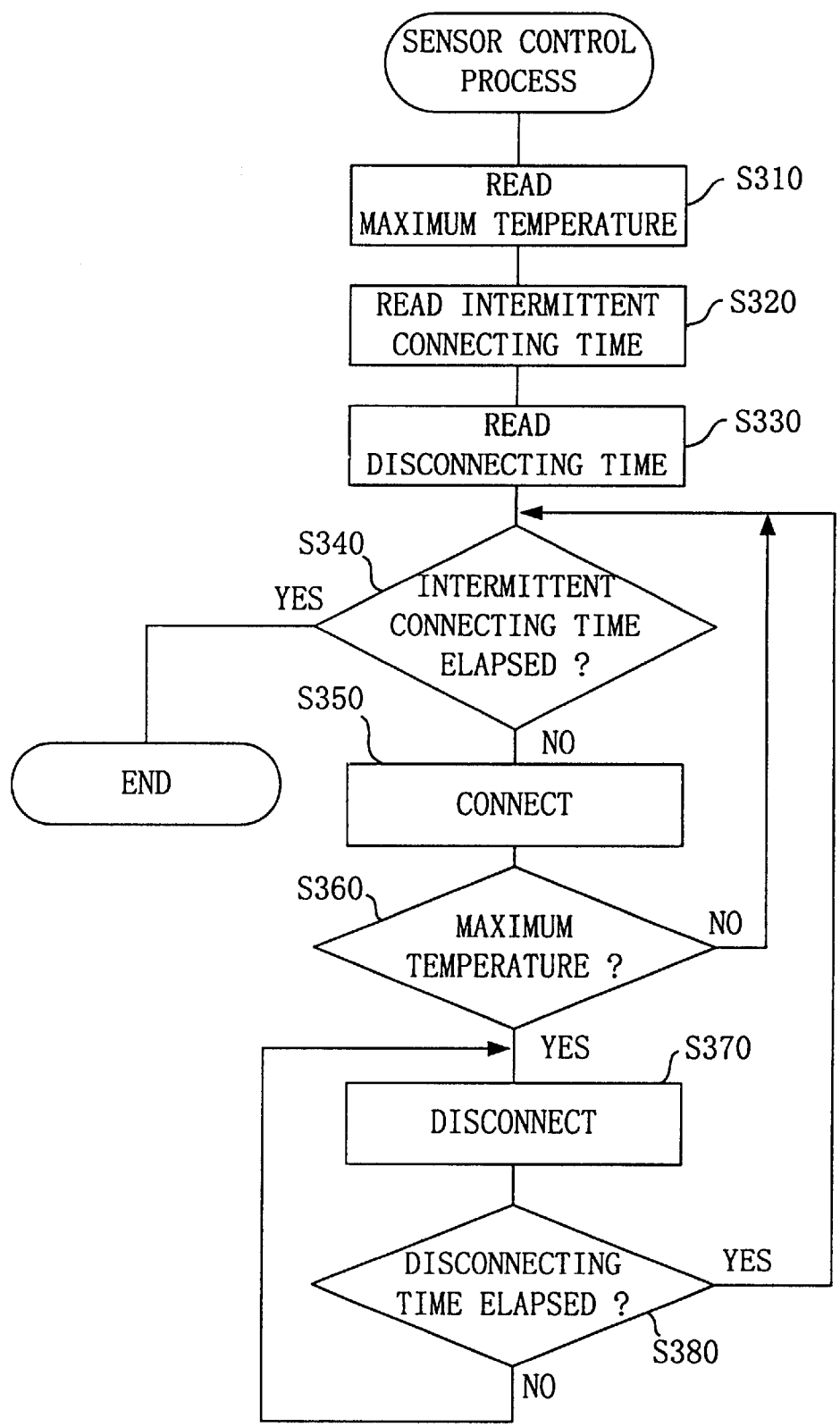
FIG. 6 is a flow chart showing an example of the sensor control process performed in the control circuit of the preferred embodiment.

When it is determined, at Step 100, that the sensor control process has been selected, the CPU 31 firstly reads, as shown in FIG. 6, a predetermined maximum temperature of the object to be heated 18 which is stored in the RAM (Step 310).

Secondly, a predetermined intermittent connecting time is read (Step 320) in the same manner as the aforementioned Step 210.

Thirdly, a predetermined disconnecting time is read (Step 330).

Then it is determined whether or not the predetermined intermittent connecting time has elapsed (Step 340). If it is determined that the predetermined intermittent connecting time has not elapsed, the current to the far infrared radiator 1 is turned "on" (Step 350). As a result, far infrared rays are radiated from the far infrared radiator 1.

Subsequently, it is determined whether or not the temperature detected by the temperature sensor 20 has reached the maximum temperature (Step 360), which maximum temperature was read at Step 310. If it is determined that the sensed temperature has not reached the maximum temperature, the process returns to Step 340 and the current to the far infrared radiator 1 is kept "on" the entire time If it is determined that the sensed temperature has reached the maximum temperature, the current to the far infrared radiator 1 is shut "off" (Step 370).

It is then determined whether (Step 380) or not the predetermined disconnecting time, read at Step 330, has elapsed and the current to the far infrared radiator 1 is kept "off" during the disconnecting time.

When it is determined that the predetermined disconnecting time has elapsed, the processes returns to and repeats Step 340. That is, the current to the far infrared radiator 1 is kept "on" until the temperature of the object to be heated 18 has reached the maximum temperature and, when it has reached the maximum temperature, heating is again stopped during the predetermined disconnecting time. When it is determined, at Step 340, that the predetermined total intermittent connecting time has eventually elapsed, the current is shut "off" and the control process ends.

As aforementioned, the object to be heated 18 is heated until its temperature has reached the maximum temperature, cooled by stopping the heating for a predetermined disconnecting time, and then heated again after the predetermined disconnecting time has elapsed until its temperature again reaches the maximum temperature. The object to be heated 18 (the user) feels this as "fluctuation" in heat, so that the user can continue undergoing treatment comfortably without becoming used to the thermal stimulation.

Figure 7:
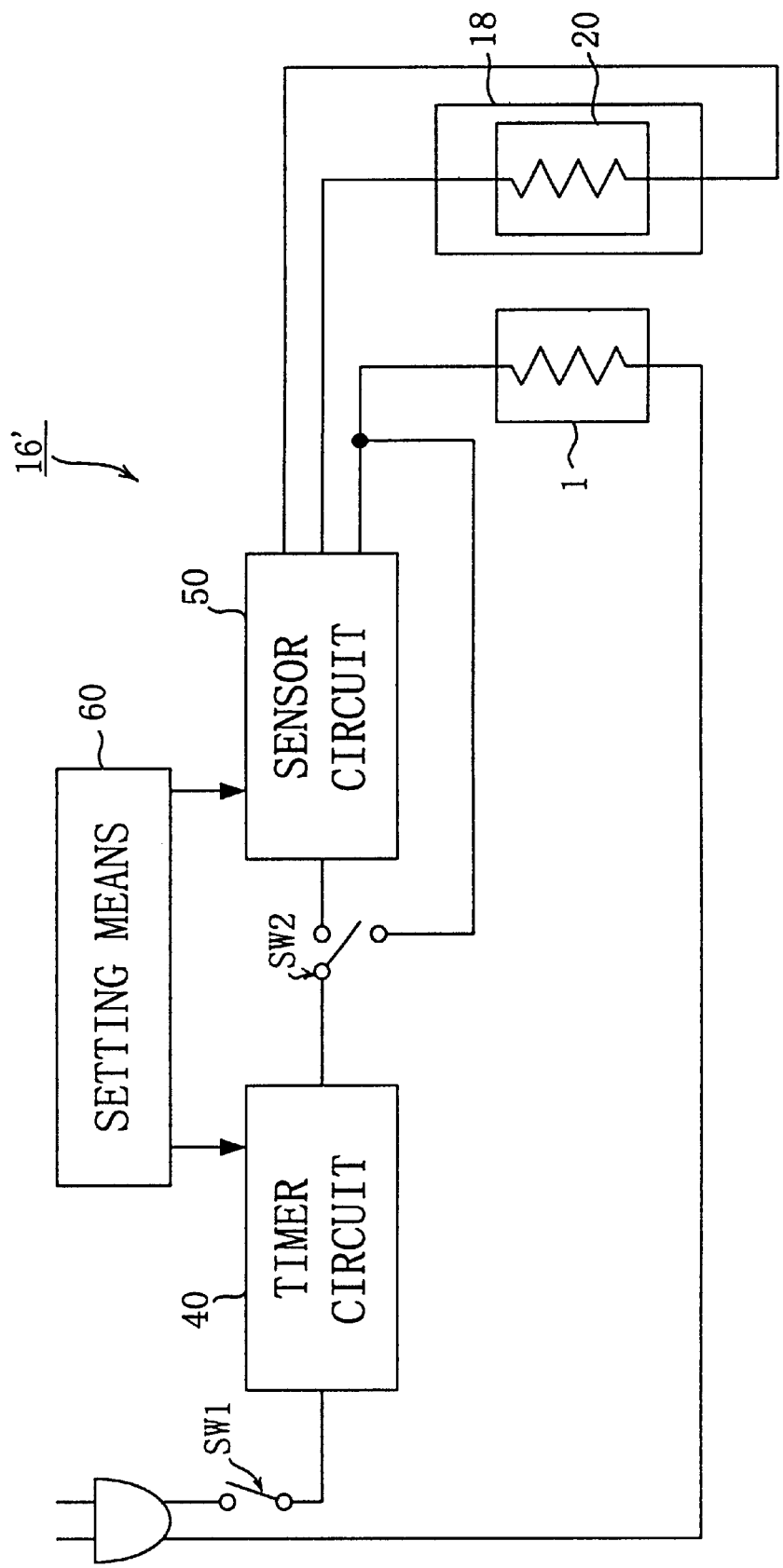
FIG. 7 is a block diagram showing a modification of the control circuit according to the present invention.

Instead of the above described computer-controlled system, a relatively simple control circuit 16, shown in FIG. 7, may be employed as a control means of the present invention.

Specifically, the control circuit 16 comprises a timer circuit 40 which performs the above described timer control process and a sensor circuit 50 which performs the above described sensor control process.

A common timer such as an electromagnetic timer may be used in the timer circuit 40. In the sensor circuit 50, a thermistor may be connected as the temperature sensor 20. In this case, the current supplied to the radiator 1 can be turned "on/off" in accordance with the resistance value of the thermistor.

In one case where the above timer control process is selected by a setting means 60, a power switch SW1 is turned "on" and a selector switch SW2 is connected to the channel by-passing the sensor circuit. Then the timer circuit 40 turns the supply of current to the radiator 1 "on/off" in accordance with an total intermittent connecting time, a connecting cycle, and the like which are all predetermined by the setting means 60.

In another case where the above sensor control process is selected by the setting means 60, the power switch SW1 is turned "on" and the selector switch SW2 is connected to the channel through the sensor circuit. In the sensor circuit 50, when the temperature sensor 20, attached to the object to be heated 18, senses a predetermined maximum temperature, the current supplied to the radiator 1 is automatically shut "off". Then, once the temperature sensor 20 senses a predetermined minimum temperature, the current supply to the radiator 1 is again turned "on".The intermittent connection to the radiator 1 is performed in this manner. In this case, timer circuit 40 counts a predetermined total intermittent connecting time set by the setting means 604 and shuts "off" the supply of current to the radiator 1 once the predetermined total intermittent connecting time has elapsed.

As described above, employment of the simple control circuit 16 can lead to the same effects as the aforementioned system with lower costs.

The invention is not restricted to the above described embodiment and may be embodied in various forms without departing from the spirit and the scope of the invention.

What is claimed is:

1. A method of treating by radiating far infrared rays from a far infrared radiator, the method comprising the steps of:

presetting control conditions of the far infrared radiator;

supplying current to the far infrared radiator for radiating the far infrared rays toward an object to be heated for a predetermined period of time;

sensing a temperature of the object to be heated with a temperature sensor;

disconnecting the supply of current to the far infrared radiator, for a predetermined disconnecting time, once the temperature of the object to be heated reaches a maximum temperature limit to interrupt the supply of the far infrared rays from the far infrared radiator;

preventing the far infrared radiator from radiating the far infrared rays toward the object to be heated until the predetermined disconnecting period of time has completely elapsed regardless of the temperature of the object to be heated; and repeating the steps of supplying current to the far infrared radiator and disconnecting the supply of current to the far infrared radiator until a predetermined time for treatment with the far infrared heating apparatus has elapsed.

2. The method according to claim 1, further comprising the steps of:

providing a timer control mode of operation for periodically interrupting the far infrared radiator from radiating the far infrared rays for the predetermined period of time;

providing a sensor control mode of operation for sensing a temperature of the object to be heated; and providing switching means for facilitating switching by a user between the sensor control mode of operation and the timer control mode of operation.

3. The method according to claim 1, further comprising the step of winding a heating wire around a bobbin to form the far infrared radiator, and coating an exterior surface of both the bobbin and the wire with a ceramic coating.

4. The method according to claim 1, further comprising the steps of:

accommodating the far infrared radiator within a housing;

accommodating a control circuit within a base; and connecting the housing to the base by a flexible support.

5. The method according to claim 1, further comprising the steps of:

providing a CPU for controlling radiation of the far infrared radiator;

providing a ROM with means for storing a control program;

providing a RAM with means for temporarily storing information;

providing an operation section with means for setting control conditions to assist with controlling the far infrared radiator;

providing an input/output interface to facilitate transmission and receipt of information to and from at least one of the far infrared radiator and the temperature sensor; and connecting the CPU, the ROM, the RAM, the operation section, the input/output interface, the far infrared radiator, and the temperature sensor to communicate with one another via a communication bus.

6. The method according to claim 5, further comprising the step of providing the operation section with a selector mechanism to facilitate selection, by an end user, of one of a timer controlled mode of operation and a sensor controlled mode of operation.

7. A method of treating by radiating far infrared rays from a far infrared radiator, the method comprising the steps of:

determining preset control conditions;

supplying current to the far infrared radiator for radiating the far infrared rays toward an object to be heated for a predetermined period of time;

sensing a temperature of the object to be heated;

disconnecting the supply of current to the far infrared radiator, for a predetermined disconnecting time, once the temperature of the object to be heated reaches a maximum temperature limit for the object to be heated to interrupt the supply of the far infrared rays from the far infrared radiator;

preventing the far infrared radiator from radiating the far infrared rays toward the object to be heated until the predetermined disconnecting period of time has completely elapsed regardless of the temperature of the object to be heated; and repeating the supply of current to the far infrared radiator and disconnecting the supply of current to the far infrared radiator steps until a predetermined time for treatment with the far infrared heating apparatus has elapsed.

8. The method according to claim 7, further comprising the steps of:

providing a timer control mode of operation for periodically interrupting the far infrared radiator from radiating the far infrared rays for the predetermined period of time;

providing a sensor control mode of operation for sensing a temperature of the object to be heated; and providing switching means for facilitating switching by a user between the sensor control mode of operation and the timer control mode of operation.

9. The method according to claim 7, further comprising the step of winding a heating wire around a bobbin to form the far infrared radiator, and coating an exterior surface of both the bobbin and the wire with a ceramic coating.

10. The method according to claim 7, further comprising the steps of:

accommodating the far infrared radiator within a housing;

accommodating a control circuit within a base; and connecting the housing to the base by a flexible support.

11. The method according to claim 7, further comprising the steps of:

providing a CPU for controlling radiation of the far infrared radiator;

providing a ROM with means for storing a control program;

providing a RAM with means for temporarily storing information;

providing an operation section with means for setting control conditions to assist with controlling the far infrared radiator;

providing an input/output interface to facilitate transmission and receipt of information to and from at least one of the far infrared radiator and the temperature sensor; and connecting the CPU, the ROM, the RAM, the operation section, the input/output interface, the far infrared radiator, and the temperature sensor to communicate with one another via a communication bus.

12. The method according to claim 11, further comprising the step of providing the operation section with a selector mechanism to facilitate selection, by an end user, of one of a timer controlled mode of operation and a sensor controlled mode of operation.

13. A method of treating by radiating far infrared rays from a far infrared radiator, the method comprising the steps of:

presetting control conditions of the far infrared radiator;

supplying current to the far infrared radiator for radiating the far infrared rays toward an object to be heated for a predetermined period of time;

disconnecting the supply of current to the far infrared radiator, for a predetermined disconnecting time, once the object to be heated has been heated for the predetermined period of time;

preventing the far infrared radiator from radiating the far infrared rays toward the object to be heated until the predetermined disconnecting period of time has completely elapsed regardless of the temperature of the object to be heated; and repeating the steps of supplying current to the far infrared radiator and disconnecting the supply of current to the far infrared radiator until a predetermined time for treatment with the far infrared heating apparatus has elapsed.

14. The method according to claim 13, further comprising the steps of:

providing a timer control mode of operation for periodically interrupting the far infrared radiator from radiating the far infrared rays for the predetermined period of time regardless of the temperature of the object to be heated;

providing a sensor control mode of operation for sensing a temperature of the object to be heated and determining when the temperature of the object to be heated reaches a predetermined maximum temperature; and providing switching means for facilitating switching by a user between the sensor control mode of operation and the timer control mode of operation.

15. The method according to claim 13, further comprising the step of winding a heating wire around a bobbin to form the far infrared radiator, and coating an exterior surface of both the bobbin and the wire with a ceramic coating.

16. The method according to claim 13, further comprising the steps of:

accommodating the far infrared radiator within a housing;

accommodating a control circuit within a base; and connecting the housing to the base by a flexible support.

17. The method according to claim 13, further comprising the steps of:

providing a CPU for controlling radiation of the far infrared radiator;

providing a ROM with means for storing a control program;

providing a RAM with means for temporarily storing information;

providing an operation section with means for setting control conditions to assist with controlling the far infrared radiator;

providing an input/output interface to facilitate transmission and receipt of information to and from at least one of the far infrared radiator and the temperature sensor; and connecting the CPU, the ROM, the RAM, the operation section, the input/output interface, the far infrared radiator, and the temperature sensor to communicate with one another via a communication bus.

18. The method according to claim 17, further comprising the step of providing the operation section with a selector mechanism to facilitate selection, by an end user, of one of a timer controlled mode of operation and a sensor controlled mode of operation.

* * * * *